(12) United States Patent
Drescher (10) Patent No.: US 8,177,851 B2
(45) Date of Patent: May 15, 2012

(54) PROSTHETIC LINER FOR AN ACETABULAR PROSTHESIS

(75) Inventor: Gerhard J. A. Drescher, Gross Pointe Park, MI (US)

(73) Assignee: DePuy Products, Inc., Warsaw, IN (US)

( * ) Notice: Subject to any disclaimer, the term of this patent is extended or adjusted under 35 U.S.C. 154(b) by 522 days.

(21) Appl. No.: 12/340,164

(22) Filed: Dec. 19, 2008
(Under 37 CFR 1.47)

(65) Prior Publication Data

US 2010/0161072 A1      Jun. 24, 2010

(51) Int. Cl.
*A61F 2/32* (2006.01)
(52) U.S. Cl. ............... 623/22.29; 623/22.24; 623/22.28
(58) Field of Classification Search .................. None
See application file for complete search history.

(56) References Cited

U.S. PATENT DOCUMENTS

| | | | |
|---|---|---|---|
| 5,989,294 A | 11/1999 | Marlow | |
| 6,162,256 A * | 12/2000 | Ostiguy et al. | 623/22.26 |
| 6,610,097 B2 | 8/2003 | Serbousek et al. | |
| 6,626,947 B2 | 9/2003 | Lester et al. | |
| 6,926,740 B2 | 8/2005 | Lewis et al. | |
| 7,108,720 B2 | 9/2006 | Hanes | |
| 7,326,253 B2 | 2/2008 | Synder et al. | |
| 2007/0106392 A1 | 5/2007 | Servidio et al. | |
| 2007/0239283 A1 | 10/2007 | Berger et al. | |

FOREIGN PATENT DOCUMENTS

| | | |
|---|---|---|
| EP | 0234811 | 9/1987 |
| FR | 2892014 | 4/2007 |

OTHER PUBLICATIONS

European Search Report in corresponding European patent application (i.e., EP 09 17 8123), dated Apr. 15, 2010 (4 pages).

* cited by examiner

*Primary Examiner* — David Isabella
*Assistant Examiner* — Brian Dukert
(74) *Attorney, Agent, or Firm* — Maginot, Moore & Beck (57) ABSTRACT

A prosthetic liner includes a convex exterior surface, a concave interior surface and a rim portion connecting the interior surface and the exterior surface. The liner includes a plurality of recesses and a plurality of fingers. Each of the plurality of recesses is formed in the exterior surface of the liner without extending to the interior surface of the liner. The plurality of fingers is positioned in the plurality of recesses and each of the plurality of fingers is connected to the exterior surface and extends toward the rim portion. The plurality of fingers may be resiliently moveable in the plurality of recesses. The plurality of fingers may be integral with the exterior surface of the liner. The rim portion may define a plane into which at least one of the plurality of fingers extends.

18 Claims, 13 Drawing Sheets

PROSTHETIC LINER FOR AN ACETABULAR PROSTHESIS

FIELD

This application relates generally to the field of orthopaedics, and more specifically to a prosthetic liner used in the hip arthroplasty.

BACKGROUND

Patients who suffer from hip pain and immobility caused by osteoarthritis and rheumatoid arthritis have an option of hip joint replacement surgery or hip joint arthroplasty in which a diseased and/or damaged hip joint is replaced with a prosthetic hip joint. In a typical hip joint arthroplasty, a proximal portion of the femur is resected and a distal portion of the acetabulum is milled. A prosthetic hip cup is attached to the acetabulum and a hip stem is attached to the femur.

Typical prosthetic hip cups include a shell or cup that is secured to milled portion of the acetabulum by bone cement, fasteners and/or features on the cup surface and a bearing or liner which includes a convex outer periphery that is secured to a concave inner periphery of the cup. Typically the liner is secured to the cup by fixed barbs on the convex outer periphery of the liner that fit into a circumferential groove positioned in the concave inner periphery of the cup. The liner, typically made of polyethylene, is pressed into the cup, typically made of metal, with the aid of a rubber mallet. During installation the barbs are deformed to pass the lip of the cup and then enter the groove of the cup. The force necessary to deform the barbs limits their size which in turn limits the securing strength of the liner to the cup. Occasionally the liner may need to be removed from the cup in situa on a patient. To remove the liner from the cup, a tool is forced between the convex outer periphery of the liner and the concave inner periphery of the cup, to pry the liner from the cup. During this removal, the barbs are again deformed to pass the lip of the cup. The force necessary to deform the barbs and the difficulty of forcing the tool between the cup and the liner makes removal of the liner from the cup in situa difficult. Therefore, it would be advantageous to provide an improved hip prosthesis.

SUMMARY

According to one embodiment of the present disclosure, there is provided a prosthetic liner. The liner includes a convex exterior surface, a concave interior surface and a rim portion connecting the interior surface and the exterior surface. The liner includes a plurality of recesses and a plurality of fingers. Each of the plurality of recesses is formed in the exterior surface of the liner without extending to the interior surface of the liner. The plurality of fingers is positioned in the plurality of recesses and each of the plurality of fingers is connected to the exterior surface and extends toward the rim portion. The plurality of fingers may be resiliently moveable in the plurality of recesses. The plurality of fingers may be integral with the exterior surface of the liner. The rim portion may define a plane into which at least one of the plurality of fingers extends.

According to another embodiment of the present disclosure, there is provided an acetabular hip system including a hip cup, a hip stem, and a liner. The liner is configured to engage the hip cup and the hip stem. The liner is includes a body portion, at least one recess, and at least one finger. The body portion includes an exterior surface configured to engage the hip cup, an interior surface configured to engage the hip stem, and a rim connecting the interior surface to the exterior surface. The recess is formed on the exterior surface and extends into the body portion without extending to the interior surface. The finger is connected to the body and is positioned in the recess.

According to another embodiment of the present disclosure, there is provided a liner for use in an orthopedic implant shell to form a hip cup to cooperate with a hip stem to form a hip prosthetic implant. The liner includes a first surface configured to cooperate with the shell, a second surface opposed to the first surface and configured for articulating cooperation with the hip stem, a rim connecting the first surface to the second surface, a first void extending into the liner from the rim and spaced from the first surface and from the second surface, and a pair of spaced apart second voids extending from the first surface to the first void. The first surface, the first void, and the pair of second voids define a finger between the first surface, the first void, and the pair of second voids. The finger is configured to assist in securing the liner to the shell. The first void may be a slot and the pair of spaced apart second voids may be slits.

Other technical advantages of the present invention will be readily apparent to one skilled in the art from the following figures, descriptions and claims.

BRIEF DESCRIPTION OF THE DRAWINGS

For a more complete understanding of the exemplary embodiments of the prosthetic liner and the advantages thereof, reference is now made to the following description taken in connection with the accompanying drawings, in which.

Corresponding reference characters indicate corresponding parts throughout the several views. Like reference characters tend to indicate like parts throughout the several views.

DETAILED DESCRIPTION OF THE PREFERRED EMBODIMENTS

Embodiments of the present invention and the advantages thereof are best understood by referring to the following descriptions and drawings, wherein like numerals are used for like and corresponding parts of the drawings.

Figure 1:
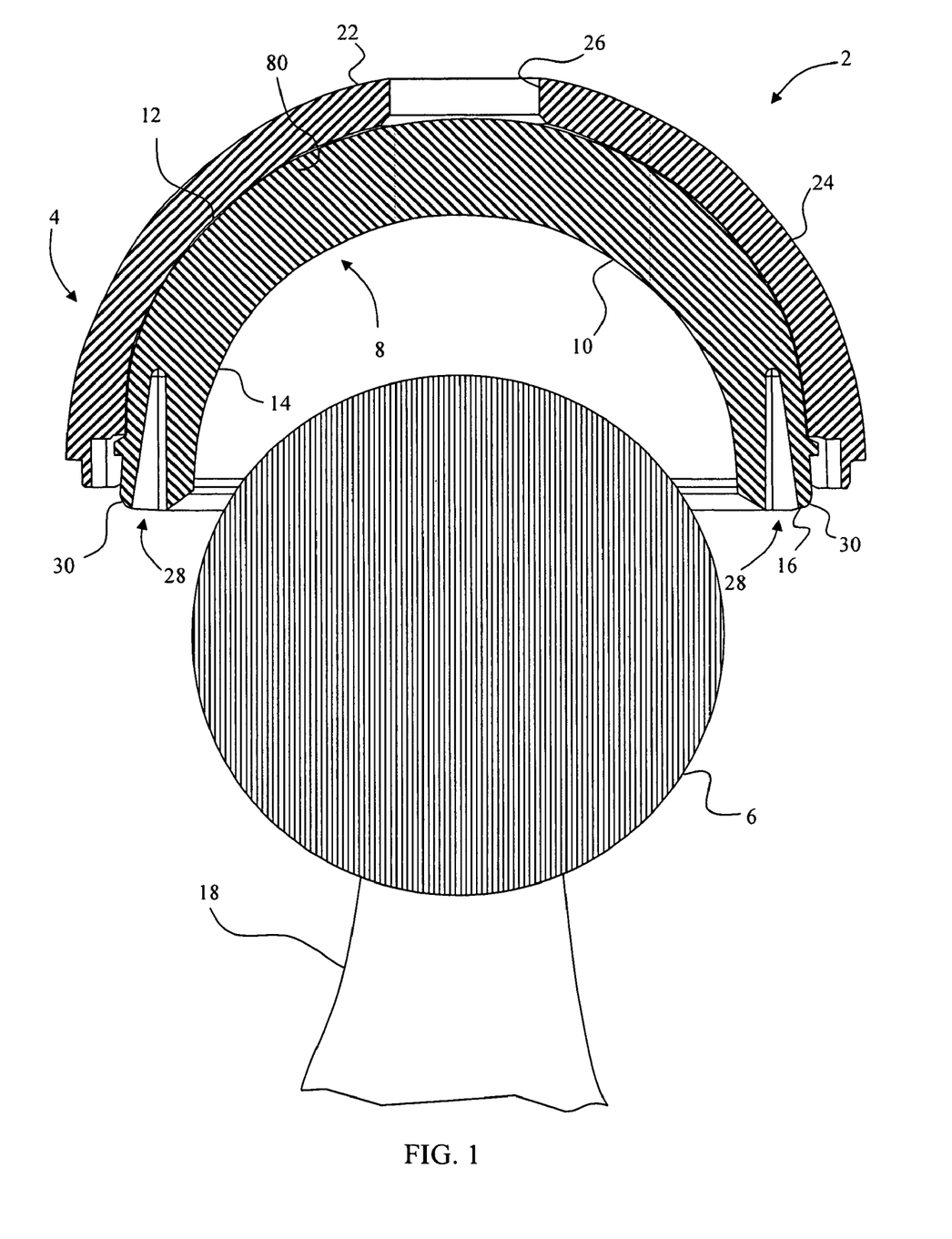
FIG. 1 depicts a cross sectional view of a liner with fingers engaged in a hip cup to form an assembly according to the present disclosure.

According to the present disclosure and referring now to FIG. 1, an acetabular hip system 2 is shown for use in hip arthroplasty. The acetabular hip system 2 includes a hip cup 4, a hip stem 6, and a liner 8. The liner 8 is configured to engage the hip cup 4 and the hip stem 6. The liner 8 includes a body portion 10 having an exterior surface 12 configured to engage the hip cup 4. The liner 8 further includes an interior surface 14 configured to engage the hip stem 6 and a rim 16 connecting the interior surface 14 to the exterior surface 12.

As shown in FIG. 1, the hip stem 6 is secured to the femur and the hip cup 4 is secured to the acetabulum. The hip cup 4 includes a convex exterior periphery 22 which may include a porous coating 24 for engagement with the acetabulum 20. The hip cup 4 may include an opening 26 to assist in separating the liner 8 from the hip cup 4 when the acetabulum hip system 2 is not in the patient.

Figure 2:
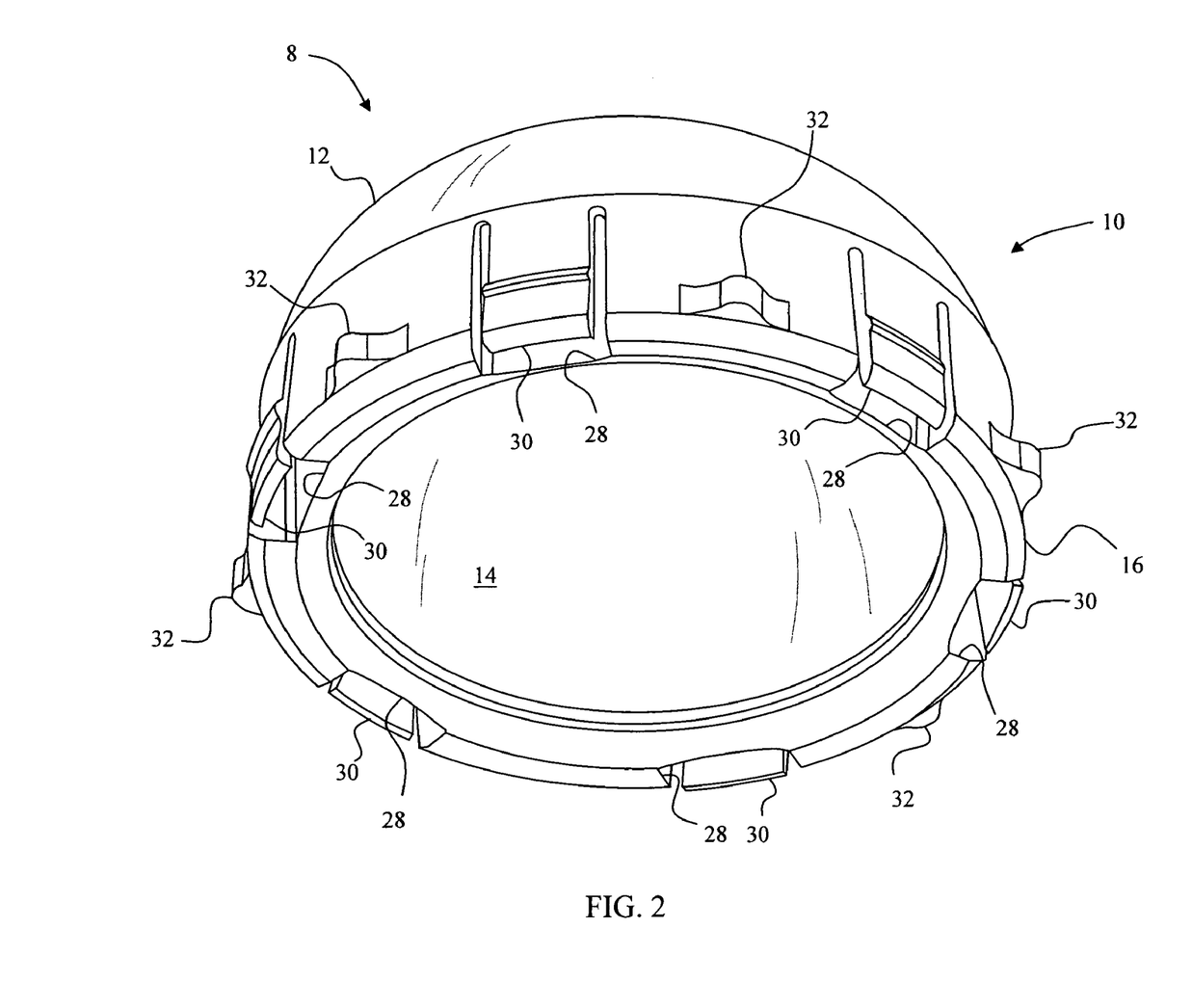
FIG. 2 depicts a perspective view of the prosthetic liner with fingers of FIG. 1.

Referring now to FIG. 2, the liner 8 is shown in greater detail. The liner 8 further includes a plurality of recesses 28 formed on the exterior surface 12 and extending into the body portion 10 of the liner 8 without extending from the exterior surface of the liner 8 to the interior surface 14. The liner 8 further includes a plurality of fingers 30 connected to the body portion 10. Each finger 30 is positioned in one of the recesses 28. The finger 30 cooperates with the hip cup 4 to secure the liner 8 to the hip cup 4.

While it should be appreciated that a single finger positioned in a single recess may be sufficient to secure the liner 8 to the hip cup 4, the liner 8 of the acetabular hip system 2 includes a plurality of fingers in the embodiment herein. Each of the fingers 30 is located in a separate one of the recesses 28 formed on the exterior surface 12. The fingers 30 and the recesses 28, as shown, are equally spaced around the rim portion 16 of the liner 8. As shown in the embodiment of FIG. 2, six spaced-apart fingers 30 are each located in one of six recesses 28 formed in the body portion 10 of the liner 8.

As shown in FIG. 2, the fingers 30 are integral with the exterior surface 12 of the liner 8. It should be appreciated that, alternatively, the fingers 30 may be made of separate components from the body portion 10 and secured to the exterior surface 12 of the body portion 10 by in a suitable manner, for example, by welding, soldering, fastening, or gluing.

The liner 8, as shown in FIG. 2, further includes a plurality of spaced-apart tabs 32 extending outwardly from the exterior surface 12 of the liner 8. The tabs 32 are, as shown, positioned between adjacent fingers 30 and, as shown in FIG. 2, a tab 32 is positioned between each of the adjacent fingers 30. As shown, the liner 8 has six equally spaced-apart tabs 32. The tabs 32 are positioned near rim 16 and are configured to engage the hip cup 4. The tabs 32 interact with the hip cup 4 to prevent undesired rotation of the liner 8 within the hip cup 4. Alternatively, other, or no, anti-rotation features may be used.

Figure 3:
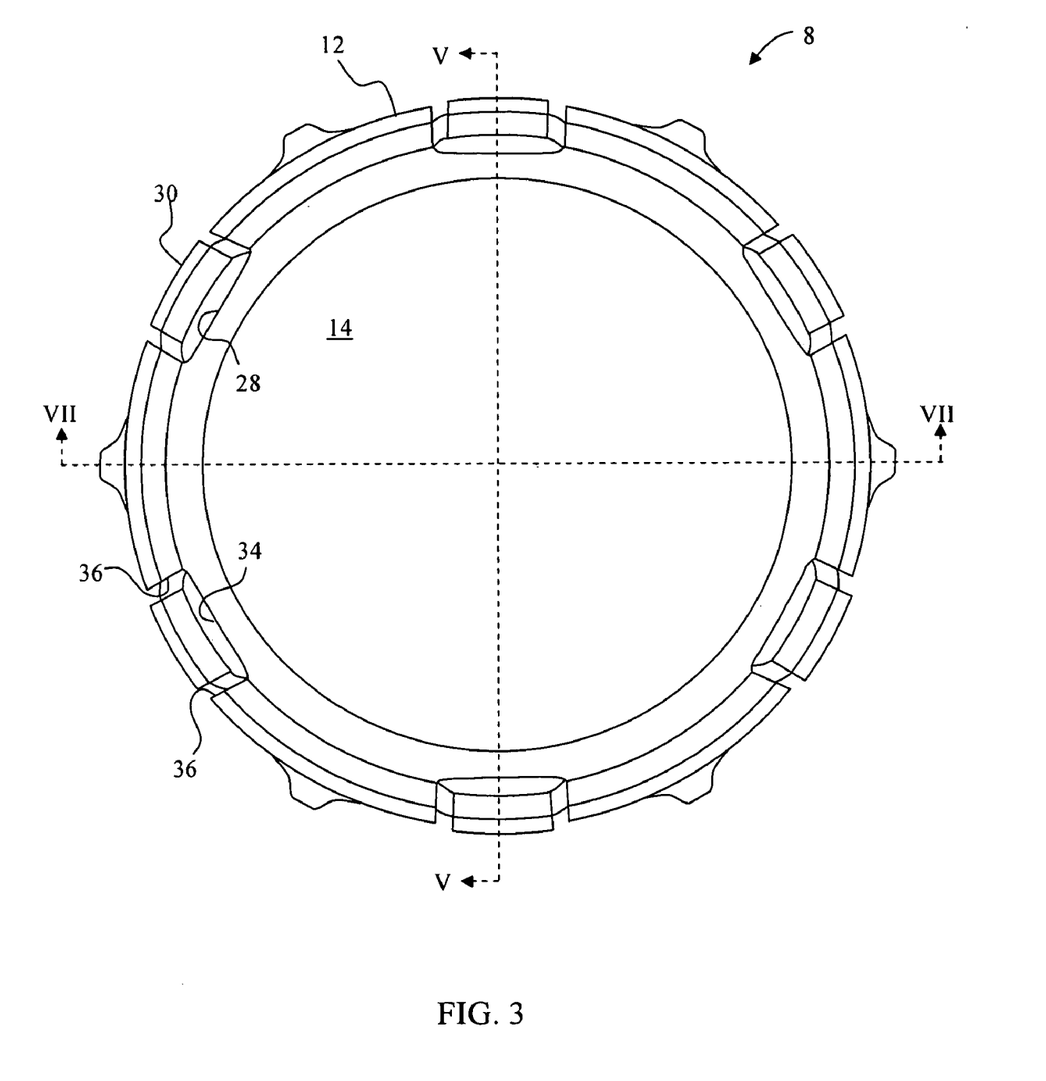
FIG. 3 depicts a bottom view of the prosthetic liner of FIG. 2 showing all the fingers in greater detail.
Figure 4:
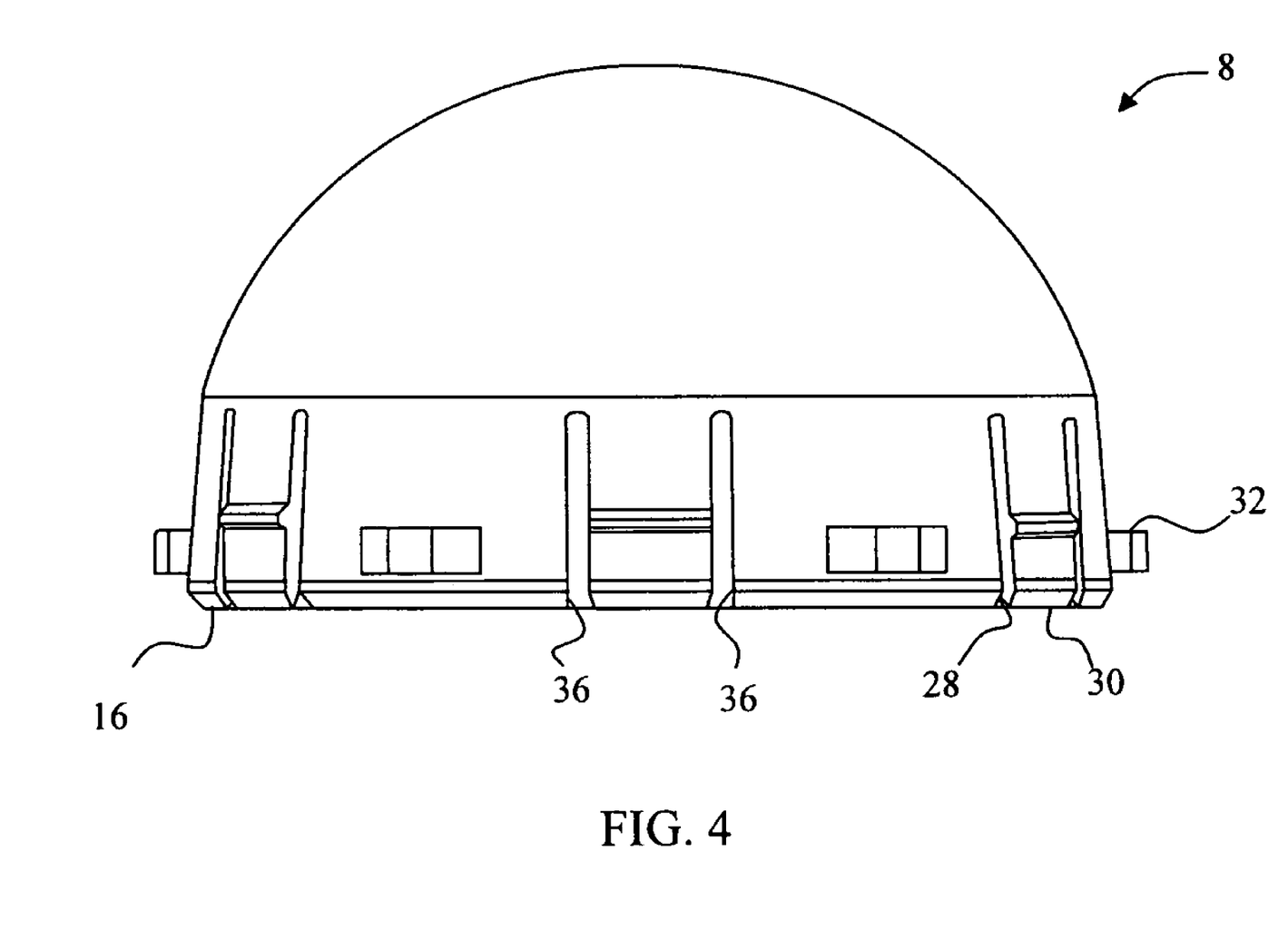
FIG. 4 depicts a plan view of the prosthetic liner of FIG. 2 showing the hemispherical portion of the liner in greater detail.

Referring now to FIGS. 3 and 4, the fingers 30 and the recesses 28 are shown in greater detail. Each recess/finger combination in the liner includes a first void 34 and a pair of spaced apart second voids 36. The first void 34 extends into the liner 8 from the rim 16 and is spaced apart from the exterior surface 12 and from the interior surface 14. Thus, the first void 34 is positioned between the finger 30 and the surface 14.

Figure 10:
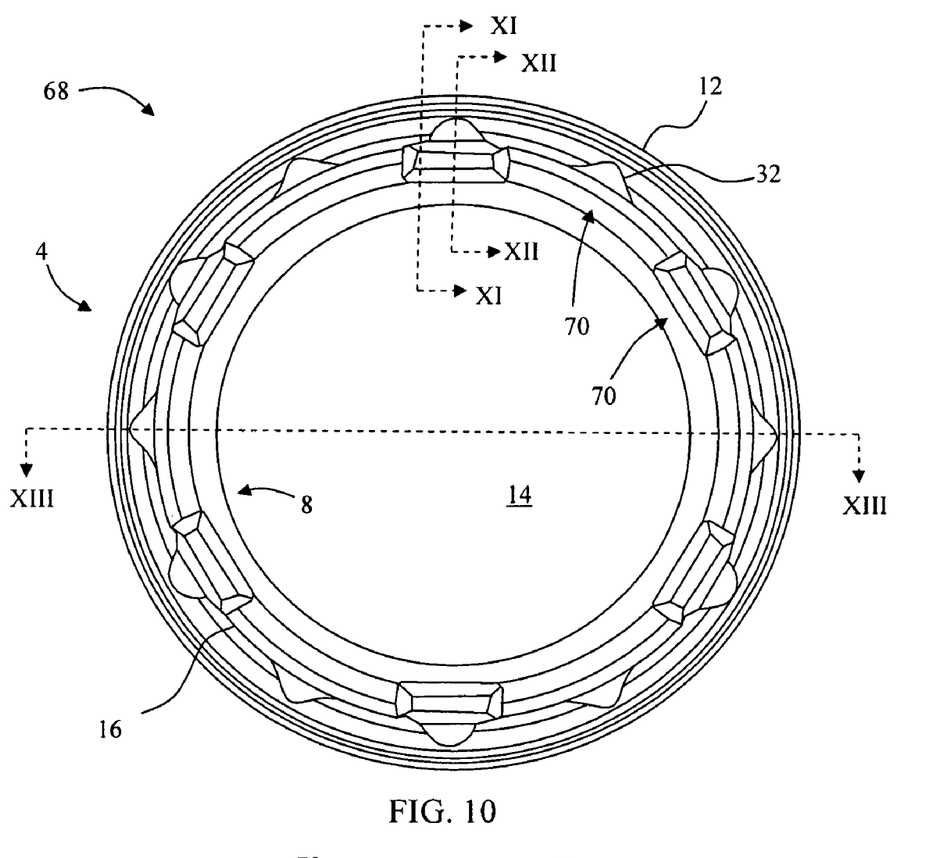
FIG. 10 depicts a bottom view of the hip prosthetic assembly of FIG. 1 showing the fingers aligned with the pockets and tabs.
Figure 10A:
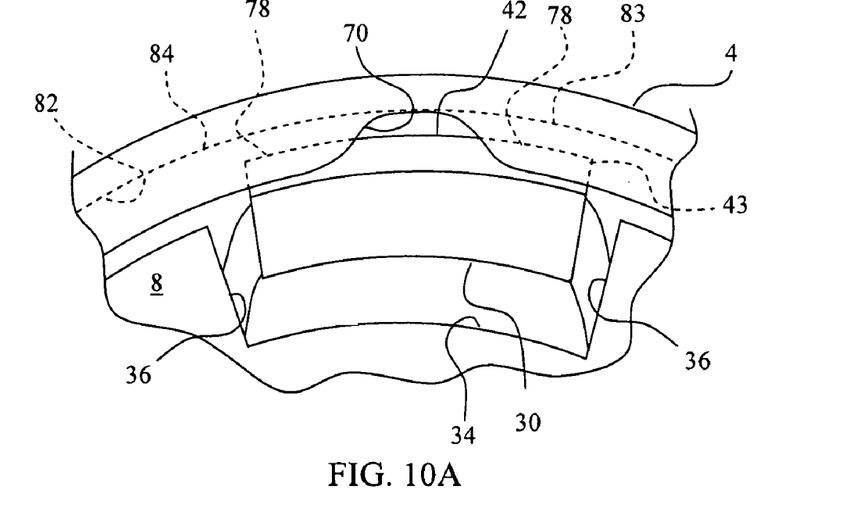
FIG. 10A is a diagrammatic bottom view showing the relationship between a finer of the liner and a pocket of the cup of the hip prosthetic assembly of FIG. 10.

With continued reference to FIGS. 3 and 4, the liner 8 further includes a pair of spaced-apart second voids 36 extending from the exterior surface 12 to the first void 34 (FIG. 10A also shows an enlarged view of the bottom of a finger 30 with first void 34 and second voids 36 adjacent to the finger 30). The exterior surface 12, the first void 34, and the pair of second voids 36 define the shape of the finger 30. The finger 30 is configured to assist in securing the liner 8 to the cup 4. The first void 34 is in the form of a slot. The pair of second voids 36 are in the form of a pair of spaced-apart slits formed in the exterior 12 of the liner 8. It should be appreciated that each of the fingers 30 are defined between a separate pair of spaced-apart second voids 36 as well as by the first void 34.

Figure 5:
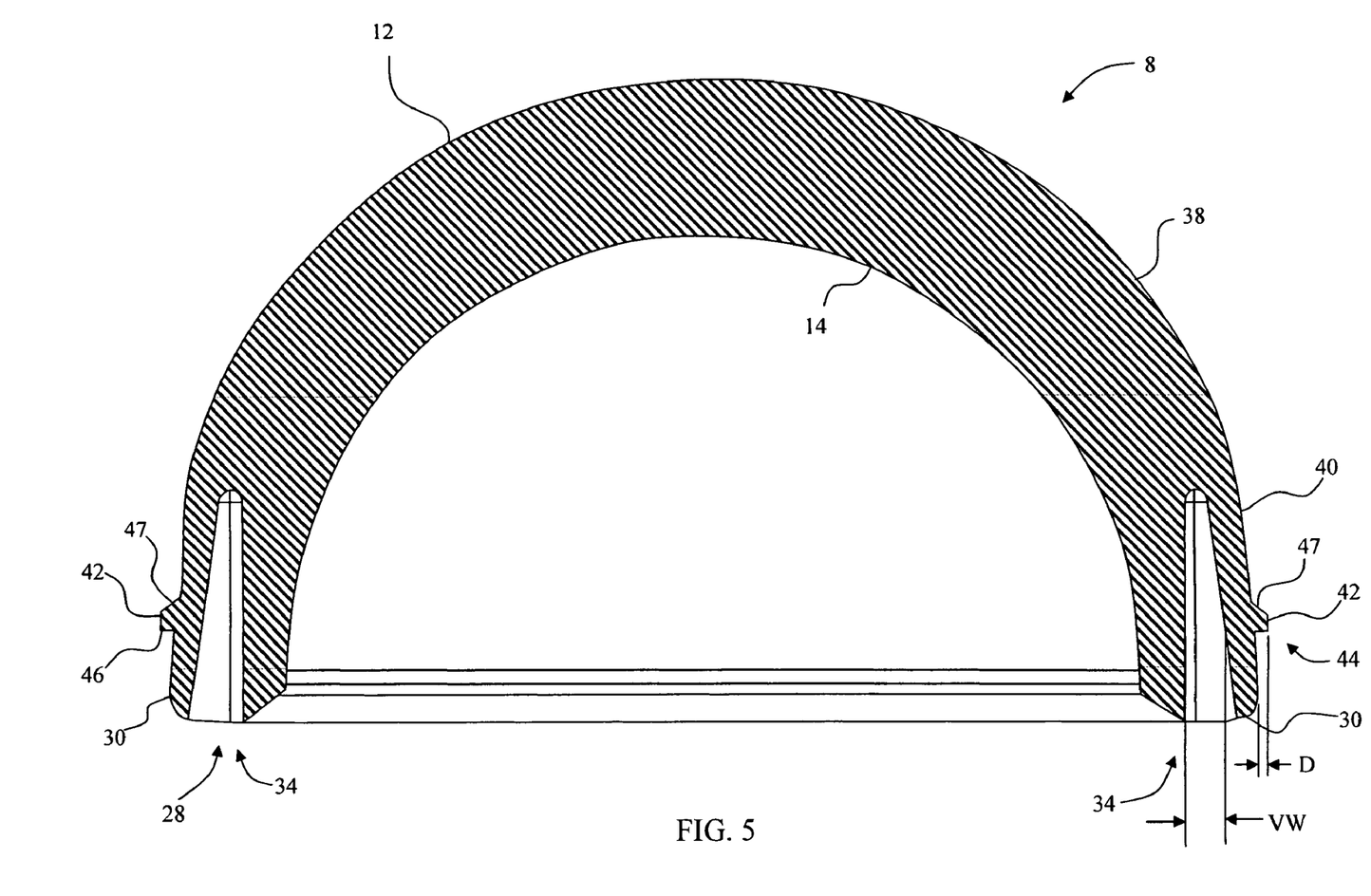
FIG. 5 depicts a cross sectional view of FIG. 3 along the line V-V in the direction of the arrows showing the shape of the liner at the fingers.

Referring now to FIG. 5, the liner 8 is shown in cross section along line V-V of FIG. 3. The exterior surface 12 of the liner 8 has a shape to conform to the hip cup 4. For example, and as shown in FIG. 5, the exterior surface 12 includes a convex exterior portion 38 and a frustroconical portion 40 extending downwardly from the convex exterior portion 38. The frustroconical portion 40 serves to align the rim 16 of the liner 8 properly with respect to the hip cup 4.

As shown in FIG. 5, each of the fingers 30 includes a protrusion 42 extending from the finger 30. The protrusion 42 defines a depth D in a direction of arrow 44 toward the interior surface 14 of the liner 8, a lower surface 46, and an opposed upper surface 47. The first void 34 defines a width VW in the direction of arrow 44. The width of the first void VW is greater than the depth D of the protrusion 42. By having the width VW greater than the depth D, the finger 30 is able to be moved in the direction of arrow 44 sufficiently to have the hip cup 4 receive the liner 8.

Figure 6:
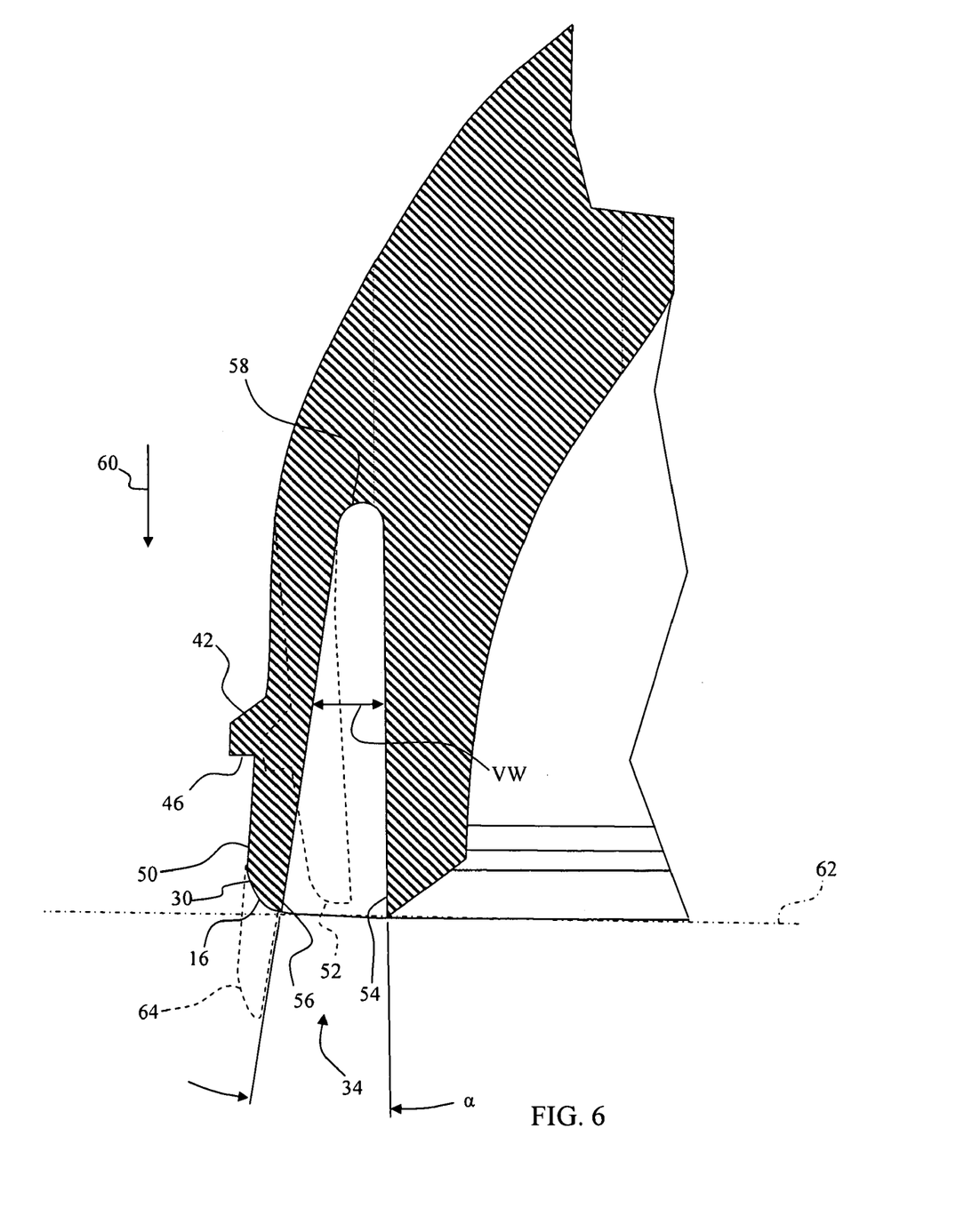
FIG. 6 depicts an enlarged partial view of FIG. 5 showing the fingers in greater detail.

Referring now to FIG. 6, the finger 30 and the first void 34 are shown in greater detail. The finger 30 may be made of a resilient material, for example, a metal or a polymer. Since the finger 30 is resilient, a force in the direction of arrow 48 causes the finger 30 to move from equilibrium position 50 to a depressed position 52 (shown by phantom lines in FIG. 6). The void 34 has a generally wedge shape defined between a first surface 54 and a second surface 56. The second surface 56 is spaced toward the external surface 12 of the liner 8. A radius portion 58 connects the first wall 54 to the second wall 56 to define the first void 34. The first wall 54 and the second wall 56 define an angle α between the walls 54 and 56. As shown in FIG. 6, the width VW of the first void 34 is progressively wider in the direction of arrow 60 toward the rim 16.

The rim 16 defines a plane 62 of the rim portion 16. The fingers 30 extend to the plane 62. It should be appreciated that the fingers may also extend past the plane 62 of the rim 16 as shown by phantom lines 64. The extended finger 64 may provide additional leverage to move the protrusion 42 and improved access to the finger 30 to remove the liner 8 from the cup 4. The protrusion 42 includes lower surface 46. As shown in FIG. 6, the lower surface 46 is parallel to the rim portion 6 or to plane 62. It should be appreciated that the surface 46 may be planar, arcuate, or another shape.

Figure 7:
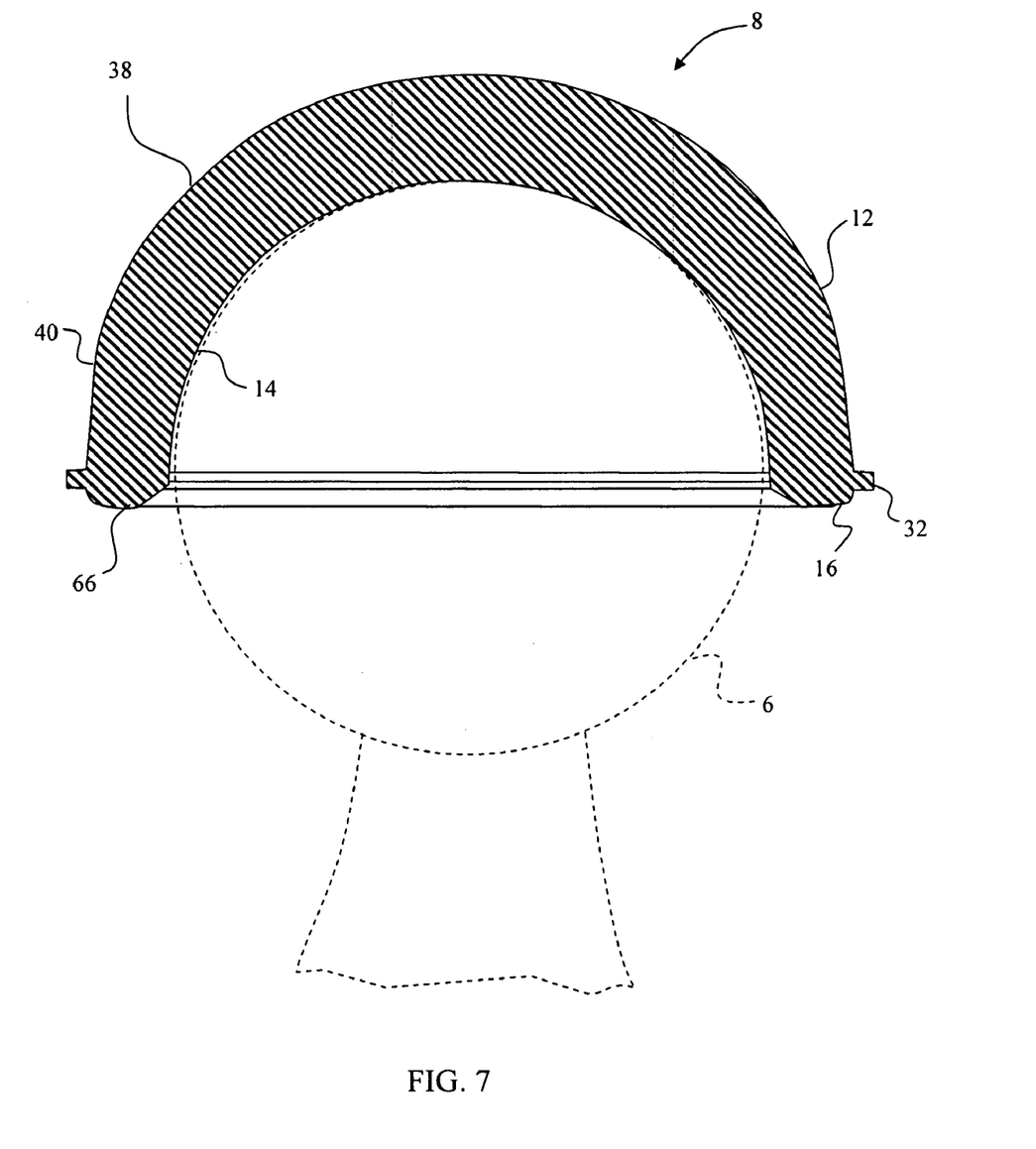
FIG. 7 depicts a cross sectional view of FIG. 3 along the line VII-VII in the direction of the arrows showing the shape of the liner spaced from the fingers.

Referring now to FIG. 7, the liner 8 is shown in cross-section, along line VII-VII of FIG. 3. The liner 38 includes the exterior surface 12, the rim 16, and the interior surface 14. The liner 8 further includes a chamfer 66, positioned between the rim 16 and the interior surface 14. The chamfer 66 serves to assist in the installation of the hip stem 6 into the prosthetic liner 8.

Figure 8:
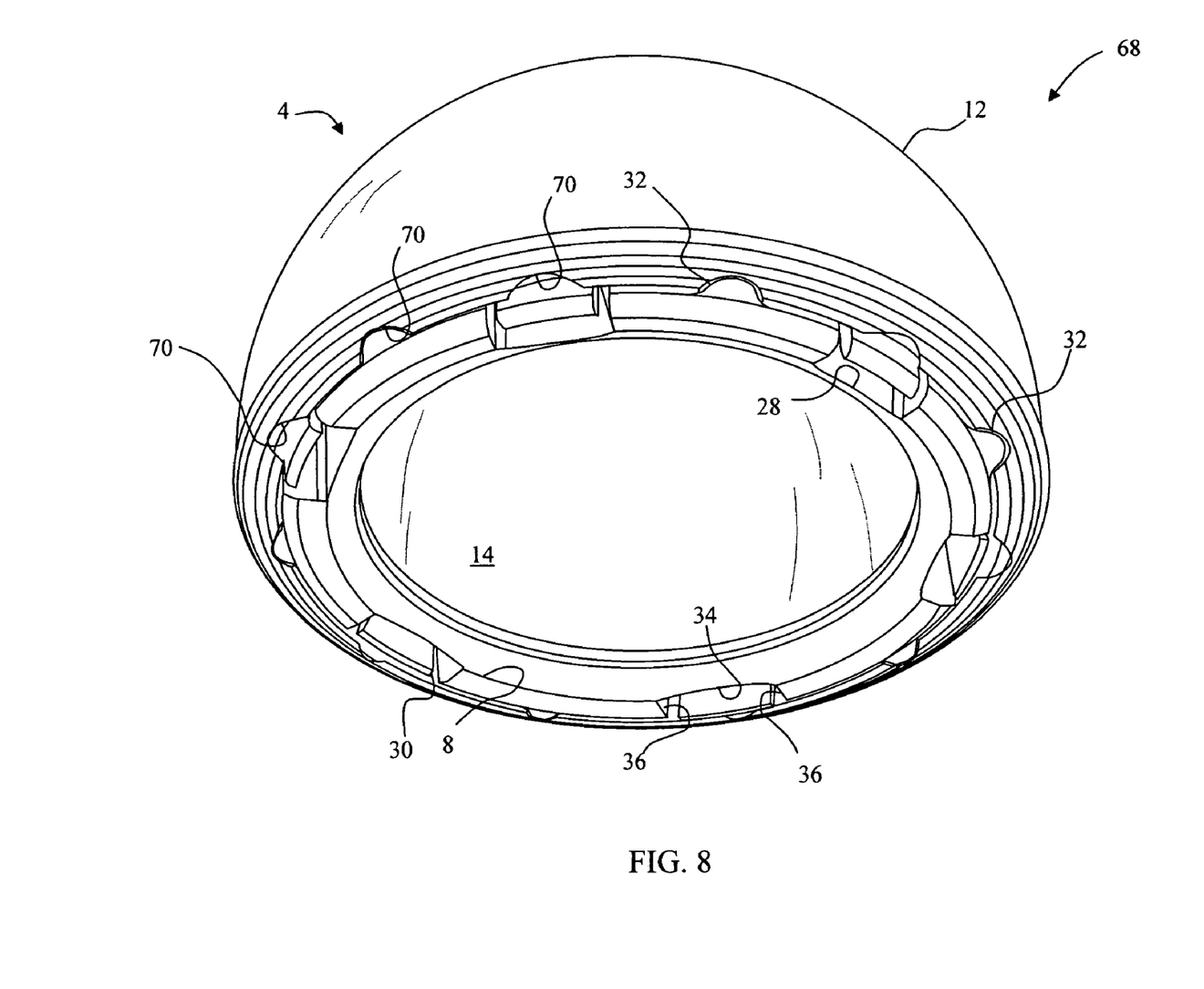
FIG. 8 depicts a perspective view of the hip prosthetic assembly of FIG. 1.

Referring now to FIG. 8, the liner 8 is shown installed in the cup 4 to form the cup liner assembly 68. The cup 4 includes a pair of spaced-apart pockets 70 for receiving the tabs 32. A separate pocket corresponds to each tab. The tabs 32 and the pockets 70 serve to angularly limit the motion of the liner 8 within the cup 4.

Figure 9:
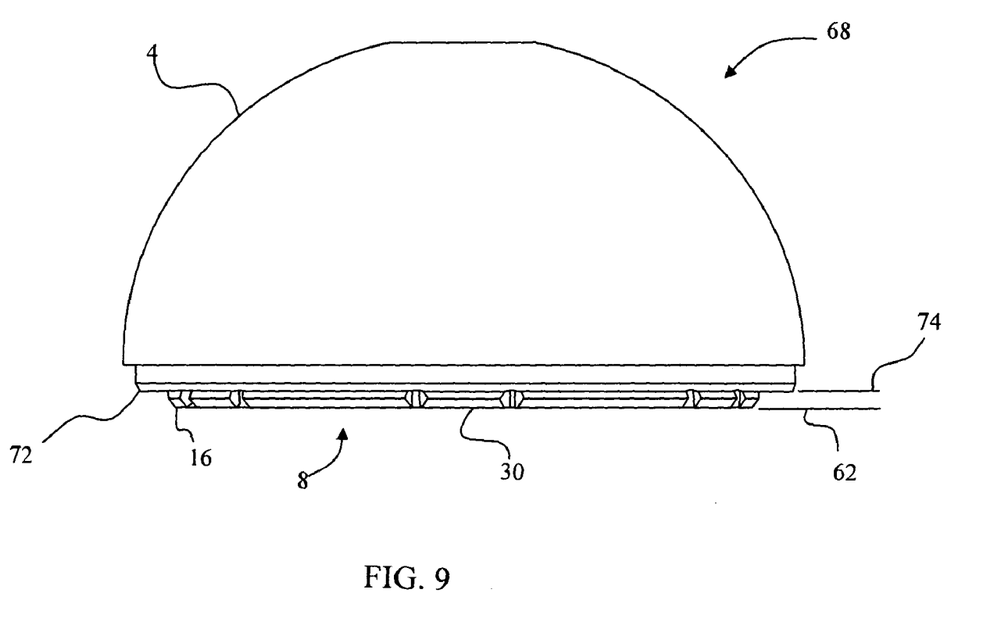
FIG. 9 depicts a plan view of the hip prosthetic assembly of FIG. 1 showing the fingers of the liner extending below the cup.

Referring now to FIG. 9, the liner 8 is shown extending from the cup 4. As shown in FIG. 9, the cup 4 includes an open-end 72. The open-end 72 defines a plane 74. As shown in FIG. 9, the rim 16 of the liner 8 extends downwardly from plane 74 of the cup 4. The positioning of the rim 16 and the fingers 30 below the plane 74 of the cup 4 permits access to the fingers 30 to permit the surgeon to deflect the fingers 30 to remove the liner 8 from the cup 4 in situa in a patient.

Referring now to FIG. 10, the open end 72 of the cup liner assembly 68 is shown in greater detail. Liner 8 is installed in the cup 4 by aligning the tabs 32 of the liner 8 with the pockets 70 of the cup 4. It should be appreciated that, as shown in FIG. 10, the liner 8 has six equally spaced tabs 32. The cup 4, however, has twelve equally spaced pockets 70. It should be appreciated that a cup (not shown) may be designed for the liner 8 and include only six pockets, with each of the pockets aligned with one of the tabs 32. The twelve pockets 70 of the cup 4 represent a commercially available hip cup in the form of a DePuy Pinnacle® Cup, a trademark of DePuy Orthopaedics, Inc., sold by DePuy Orthopaedics, Inc., Warsaw, Ind. In revision surgery, the liner 8 of the present disclosure may be inserted into the Pinnacle® Cup with the six tabs 32 of the liner 8 engaging six of the pockets 70 in the cup 4, and the six fingers 30 of the liner 8 engaging the remaining six pockets 70 in the cup. In an alternative embodiment, the fingers may be configured on the liner 8 for positioning between the pockets 70 rather than engaging the pockets.

FIG. 10A shows a bottom view of one of the fingers 30 of the liner 8 positioned in abutment with a pocket 70 of the cup 4. FIG. 10A is a see-through view to the protrusion 42 of the finger 30. In particular, the dotted lines 43 in FIG. 10A represent the edges of the protrusion 42 of the finger 30. The protrusion 42 of the finger 30 engages the cup 4 within the groove 82. The outer wall 84 of the groove 82 is represented by dotted lines 83 in the see-through view of FIG. 10A. The protrusion 42 of the finger 30 is positioned within the pocket 70 and extends past the pocket 70 into the groove 82 of the liner at engaging areas 78 adjacent to the pocket 70. In particular, the engaging areas 78 show where the protrusion 42 engages with the groove 82 of the cup 4. The pockets 70 in the embodiment of FIG. 10A reduce the engaging area 78. However, it should be appreciated that in an alternative embodiment, the cup may not have pockets, or may have smaller pockets, such that the protrusions 42 would have larger engaging areas with the groove 82 of the cup 4.

Figure 11:
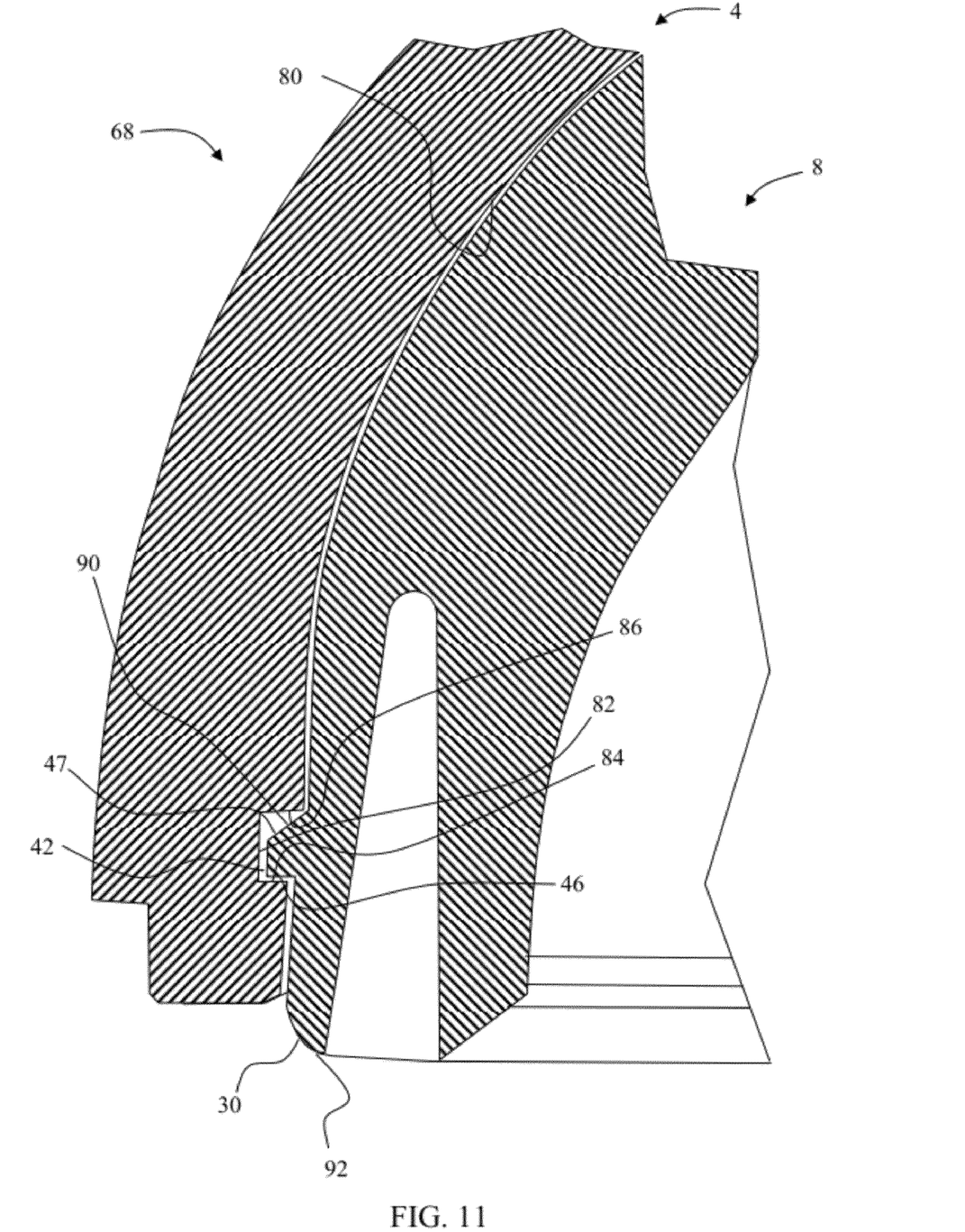
FIG. 11 depicts an enlarged partial cross sectional view of FIG. 10 along the line XI-XI in the direction of the arrows showing one of the fingers in engagement with the circumferential groove of the cup.

Referring now to FIG. 11, the cup liner assembly 68 is shown in cross-section along line XI-XI of FIG. 10. This Figure shows the engagement of the protrusion 46 of the finger 30 of the liner 8 with the cup 4 in greater detail. As shown in FIG. 11, the cup 4 includes a circumferential groove 82 extending into the cup 4 from the internal periphery 80 of the cup 4. The circumferential groove 82 is fitted to receive protrusion 42 of the finger 12. The circumferential groove 82 includes a lower wall 84 that cooperates with lower surface 46 of the protrusion 42 to secure the liner 8 within the cup 4. In particular, lower wall 84 abuts lower surface 46 of the protrusion 42 when the liner is fully seated in the cup. The circumferential groove 82 further includes an upper wall 86 that is spaced from upper surface 47 of the protrusion 42 of the finger 30 of the liner 8. The upper surface 47 of the protrusion 42 includes a chamfer 90. When the finger 30 is in engaged position 92, as shown in solid, the liner 8 is securely attached to the cup 4.

Figure 12:
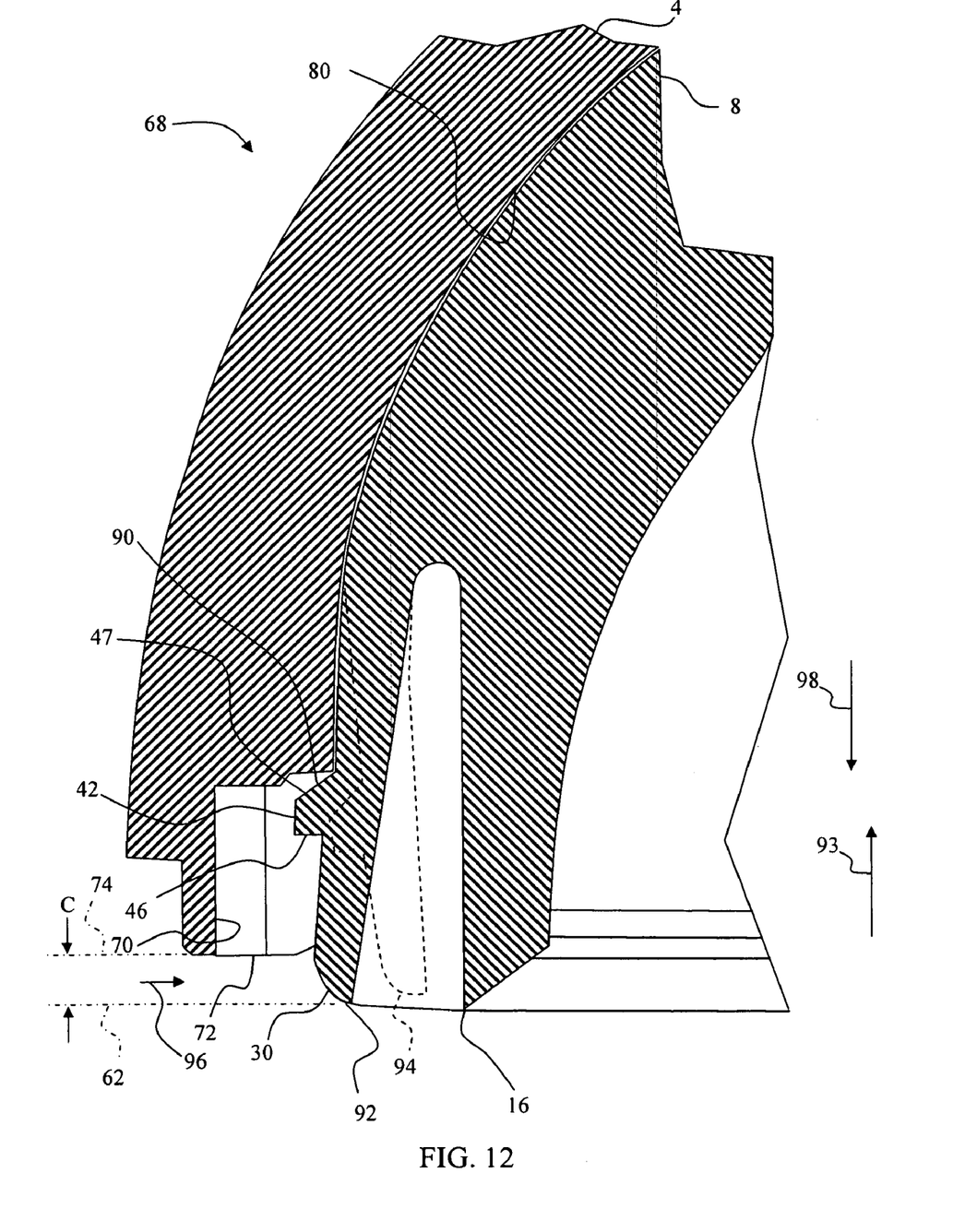
FIG. 12 depicts is an enlarged partial cross sectional view of FIG. 10 along the line XII-XII in the direction of the arrows showing one of the fingers positioned in one of the pockets of the cup.

Referring now to FIG. 12, the protrusion 42 of liner 8 is shown in the pocket 70 of cup 4. The liner 8 is inserted into the cup 4 in the direction of arrow 93. The chamfer 90 of the upper surface 47 of the finger 30 cooperates with the open end 72 and the inner periphery 80 of the cup 4 as the liner 8 is inserted into the cup 4. The chamfer 90 assist in urging the finger 30 from a relaxed position (not shown) that is similar to engaging position 92, as shown in solid, to depressed position 94, as shown in phantom. When the protrusion 46 is aligned with the circumferential groove 82, the protrusion 46 enters the groove 82 and the finger moves from the depressed position 94 to the engaged position 92.

Continuing to refer to FIG. 12, to remove the liner 8 from the cup 4 in situa on a patient, the surgeon may place his fingers against finger 30 of the liner 8. The plane 62 of rim 16 of liner 8 extends a distance C from the plane 74 of open end 72 of cup 4, exposing the fingers 30 and permitting the surgeon to reach the fingers 30 with the cup 4 implanted in the patient. The surgeon moves the fingers 30 in the direction of arrow 96 from engaged position 92 to depressed position 94. Once the fingers 30 are depressed, the surgeon may then move the liner 8 in the direction of arrow 98, removing the liner 8 from the cup 4. As further explanation, if the finger 30 shown in FIG. 11 is considered in a similarly depressed position to that shown in FIG. 12, it can be clearly seen that the of the protrusion 42 of the finger 30 will be removed from the groove 82 when in the depressed position, allowing the liner 8 to be removed from the cup 4. To facilitated removal, the surgeon may simultaneously depress each of the six fingers 30, prior to removing the liner 8 in the direction of arrow 98. It should be appreciated that a liner with as few fingers as needed may further facilitate ease the removal of the liner 8 from the cup 4.

Figure 13:
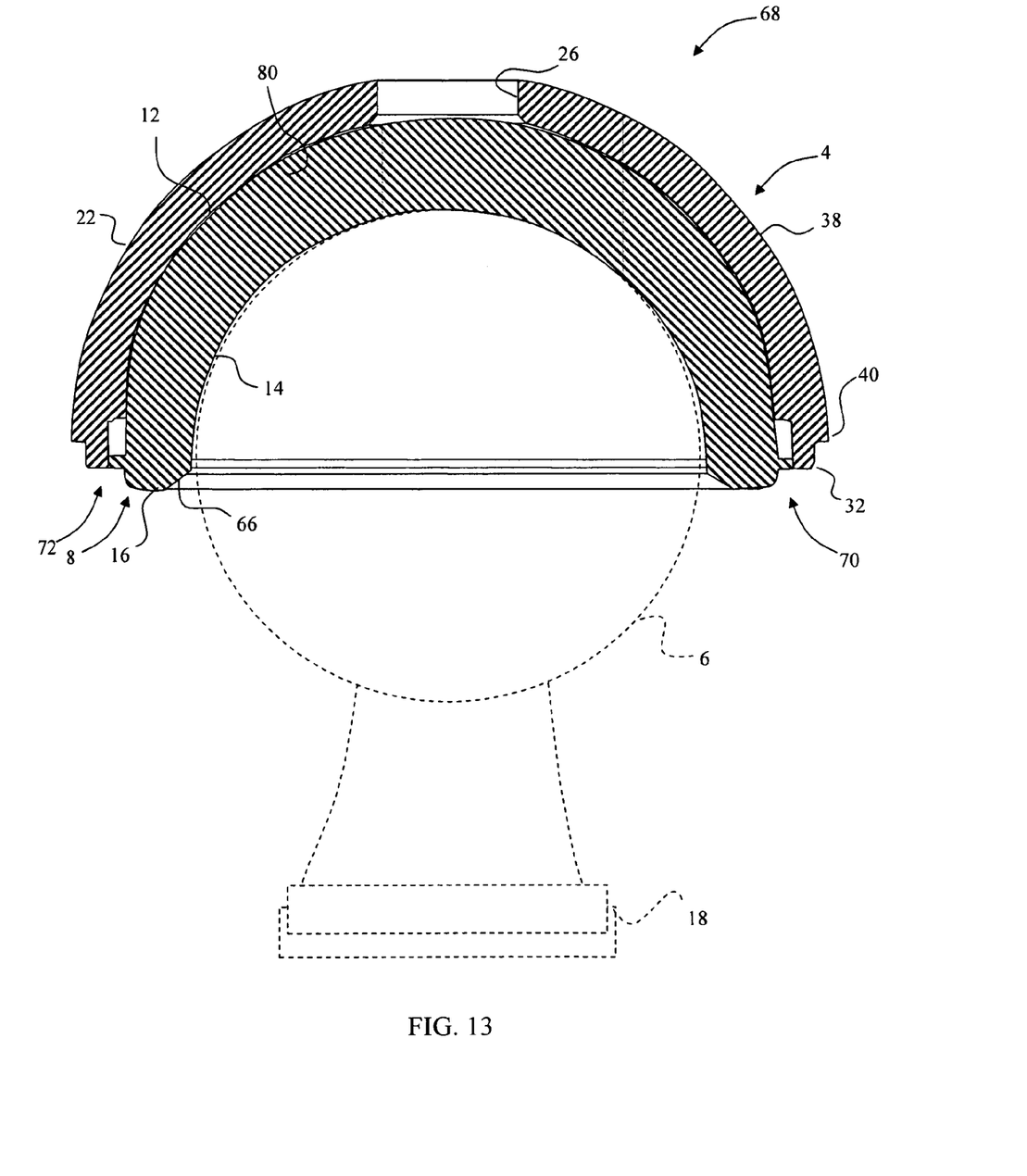
FIG. 13 depicts a cross sectional view of FIG. 10 along the line XIII-XIII in the direction of the arrows showing the shape of the liner and cup spaced from the fingers.

Referring now to FIG. 13, the cup liner assembly 68 is shown in cross section along line XIII-XIII of FIG. 10, with the stem 6 and a femur shown in dotted lines. The cup liner assembly 68 includes the cup 4 having an internal periphery 80 that matches with external periphery 12 of the liner.

Of course, numerous other adaptations are possible. Moreover, there are advantages to individual advancements described herein that may be obtained without incorporating other aspects described above. Therefore, the spirit and scope of the appended claims should not be limited to the description of the preferred embodiments contained herein.

We claim:

1. A prosthetic liner, said liner comprising:
a convex exterior surface;
a concave interior surface;
a rim portion connecting the interior surface and the exterior surface at a bottom portion of the liner, said rim portion defining a lower plane thereof;
a plurality of recesses, each of the plurality of recesses formed in the exterior surface of the liner without extending to the interior surface of the liner; and
a plurality of fingers, each of the plurality of fingers (i) positioned in a respective one of the plurality of recesses, (ii) connected to the exterior surface, and (iii) extending downwardly from the exterior surface within the respective one of the plurality of recesses, wherein at least one of said plurality of fingers extends into the lower plane of the rim portion.

2. The liner of claim 1, wherein at least one of the plurality of fingers includes a protrusion extending outwardly therefrom.

3. The liner of claim 2, wherein the protrusion includes a surface substantially parallel to the rim portion.

4. The liner of claim 1, wherein at least one of the plurality of fingers is spaced apart from an inner wall of the respective one of the plurality of recesses by a first distance in a first plane, the first plane substantially parallel to a second plane defined by the rim portion and.

5. The liner of claim 4,
wherein the at least one of the plurality of fingers includes a protrusion extending therefrom, the protrusion extending outwardly in the first plane from the at least one of the plurality of fingers by a second distance; and
wherein the first distance is greater than the second distance.

6. The liner of claim 4, wherein the plurality of fingers are resiliently moveable in the plurality of recesses.

7. The liner of claim 4, wherein the recess is generally wedge-shaped between the interior surface and the exterior surface.

8. The liner of claim 1, wherein the plurality of fingers are integral with the exterior surface of the liner.

9. An acetabular hip system comprising:
a hip cup;
a hip stem; and
a liner configured to engage the hip cup and the hip stem, the liner comprising,
a body portion including an exterior surface configured to engage the hip cup, an interior surface configured to engage the hip stem, a rim connecting the interior surface to the exterior surface at a bottom portion of the liner, said rim defining a lower plane thereof,
a first recess formed on the exterior surface and extending into the body portion without extending to the interior surface, and
a first finger connected to the body portion and positioned in the first recess, wherein at least a portion of the first finger is located directly beneath a portion of the body portion, wherein said first finger extends into the lower plane of the rim.

10. The hip system of claim 9, wherein the first finger includes an outwardly extending protrusion having a maximum radial width.

11. The hip system of claim 10:
wherein a void is defined in the first recess between the first finger and the body and spaced apart from said exterior surface, the void defining a maximum radial width thereof; and
wherein the maximum radial width of the void is greater than the maximum radial width of the protrusion.

12. The hip system of claim 11, wherein the first finger is resiliently moveable into a portion of the void.

13. The hip system of claim 9, further comprising a second finger connected to the body portion, the second finger positioned in a second recess.

14. The hip system of claim 9:
wherein a void is defined between the first finger and the body; and
wherein the void is continuously progressively deeper in the direction toward the rim.

15. A liner for use in an orthopedic implant shell to form a hip cup to cooperate with a hip stem to form a hip prosthetic implant, said liner comprising:
a first surface configured to cooperate with the shell;
a second surface opposed to the first surface and configured for articulating cooperation with the hip stem;
a rim connecting the first surface to the second surface;
a first void extending upwardly into the liner from the rim and spaced from the first surface and from the second surface; and
a pair of spaced apart second voids extending upwardly from the rim and inwardly from the first surface to the first void, the first void and the pair of second voids defining a finger therebetween, the finger configured to assist in securing said liner to the shell.

16. The liner of claim 15, wherein the finger includes a protrusion extending outwardly therefrom.

17. The liner of claim 15, wherein the first void comprises a slot.

18. The liner of claim 15, wherein the pair of spaced apart second voids comprises a pair of spaced apart slits.

* * * * *